United States Patent
Zhao et al.

(10) Patent No.: US 11,007,298 B2
(45) Date of Patent: May 18, 2021

(54) MODIFIED BIODEGRADABLE AND MEDICAL POLYMER DEVICES AND A METHOD FOR PREPARING THE SAME

(71) Applicant: Beijing Advanced Medical Technologies, Inc., Beijing (CN)

(72) Inventors: Hugh Qinghong Zhao, Pleasanton, CA (US); Qing Liu, Beijing (CN); Hanqing Feng, Beijing (CN); Guixin Shi, Boucherville (CA); Dengqiang Jia, Beijing (CN)

(73) Assignee: Beijing Advanced Medical Technologies, Ltd. Inc., Beijing (CN)

( * ) Notice: Subject to any disclaimer, the term of this patent is extended or adjusted under 35 U.S.C. 154(b) by 108 days.

(21) Appl. No.: 16/098,421

(22) PCT Filed: May 4, 2016

(86) PCT No.: PCT/CN2016/080971
§ 371 (c)(1),
(2) Date: Nov. 1, 2018

(87) PCT Pub. No.: WO2017/190290
PCT Pub. Date: Nov. 9, 2017

(65) Prior Publication Data
US 2020/0306409 A1    Oct. 1, 2020

(51) Int. Cl.
| A61L 17/12 | (2006.01) |
| A61L 17/00 | (2006.01) |
| A61L 31/06 | (2006.01) |
| A61L 31/14 | (2006.01) |
| A61L 31/16 | (2006.01) |
| C08L 67/04 | (2006.01) |

(52) U.S. Cl.
CPC ............ *A61L 17/12* (2013.01); *A61L 17/005* (2013.01); *A61L 31/06* (2013.01); *A61L 31/148* (2013.01); *A61L 31/16* (2013.01); *C08L 67/04* (2013.01); *A61L 2300/21* (2013.01); *A61L 2300/606* (2013.01); *C08L 2203/02* (2013.01); *C08L 2205/025* (2013.01)

(58) Field of Classification Search
CPC ...... A61L 17/12; A61L 17/005; A61L 31/148; A61L 31/16; A61L 31/06; A61L 2300/21; A61L 2300/606; C08L 67/04; C08L 2203/02; C08L 2205/025
USPC ........................................................ 524/291
See application file for complete search history.

(56) References Cited

U.S. PATENT DOCUMENTS

| 5,180,765 A | 1/1993 | Sinclair | |
| 8,183,427 B2* | 5/2012 | Belenkaya | ............... D01F 6/92 602/48 |
| 9,486,338 B2* | 11/2016 | McClain | ................ A61L 31/06 |
| 2006/0147491 A1* | 7/2006 | DeWitt | .................... A61L 31/10 424/426 |
| 2008/0097580 A1 | 4/2008 | Dave | |

FOREIGN PATENT DOCUMENTS

| CA | 497830 | 11/1953 |
| WO | WO-0243799 A1 | 6/2002 |
| WO | WO-2006074391 A2 | 7/2006 |
| WO | WO-2006074406 A2 | 7/2006 |

OTHER PUBLICATIONS

Snejdrova et al. "Mucoadhesive plasticized system of branched poly(lactic-co-glycolic acid) with acyclovir", Drug Development and Industrial Pharmacy (2016), 42(10), 1653-1659. (Year: 2016).*
"European Application Serial No. 16900812.5, Response Filed May 29, 2019 to Communication pursuant to Rules 161(2) and 162 EPC dated Dec. 11, 2018", 5 pgs.
"European Application Serial No. 16900812.5, Extended European Search Report dated Nov. 28, 2019", 7 pgs.
"International Application Serial No. PCT/CN2016/080971, International Search Report dated Jan. 26, 2017", 3 pgs.
"International Application Serial No. PCT/CN2016/080971, Written Opinion dated Jan. 26, 2017", 5 pgs.
"International Application Serial No. PCT CN2016 080971, International Preliminary Report on Patentability dated Nov. 15, 2018", 7 pgs.
European Application Serial No. 16900812.5, Response filed May 21, 2020 to Extended European Search Report dated Nov. 28, 2019, 6 pgs.

* cited by examiner

*Primary Examiner* — Michael Bernshteyn
(74) *Attorney, Agent, or Firm* — Schwegman Lundberg & Woessner, P.A.

(57) ABSTRACT

A medical polymer device comprising a biodegradable polymer is provided, wherein the biodegradable polymer has a crystallinity of about 10% to about 80%, and preferably from about 20% to about 60%, wherein the medical polymer device comprises a small molecule organic compound which diffuses into the biodegradable polymer, the small molecule organic compound has a molecular weight of from about 100 to about 1000 Daltons, preferably from about 150 to about 500 Daltons, and more preferably from about 150 to about 250 Daltons, and the small molecule organic compound is non-evaporating or low-evaporating. The present invention also provides a method for preparing a medical polymer device according to the present invention as well as a method for modifying a medical polymer device made from a biodegradable polymer.

15 Claims, 3 Drawing Sheets

MODIFIED BIODEGRADABLE AND MEDICAL POLYMER DEVICES AND A METHOD FOR PREPARING THE SAME

CROSS-REFERENCE TO RELATED APPLICATIONS

This application is a U.S. National Stage Filing under 35 U.S.C. 371 from International Application No. PCT/CN2016/080971, filed on May 4, 2016, and published as WO 2017/190290 A1 on Nov. 9, 2017, which is incorporated by reference herein in its entirety.

TECHNICAL FIELD

The present invention belongs to the field of medical materials and devices, and in particular describes medical polymer devices having improved mechanical properties and a method for preparing the medical polymer devices.

BACKGROUND ART

The use of biodegradable polymers and their devices in the regenerative medicine or tissue engineering field has been a common practice nowadays. One of the major advantages of using the biodegradable polymers is that the polymer or its device will be completely eliminated from human body after fulfilling its intended function(s).

Mechanical properties are important considerations when a biodegradable polymer is chosen for an intended application. For example, a surgical suture made from a biodegradable polymer needs to have enough tensile strength to keep the wound close for a certain period of time. Both a biodegradable bone screw and a biodegradable bone plate need to have enough compression and bending strengths to withstand the physiological load from the body and/or body movement. A biodegradable stent will need to have enough radial strength to keep blood vessel open, et al.

Traditionally, there are several ways to modify the mechanical properties of a polymer. They are as follows: 1) blending with another polymer; 2) copolymerization with another monomer to form a new copolymer; and 3) using a filler or fiber to reinforce the polymer. All these methods are quite effective in most cases. However, these methods require expensive equipments to synthesis or process the polymers and/or composites comprising the polymers. Also, these methods are quite difficult and/or very time consuming to implement.

For a crystalline polymer, the crystallinity played an important role in determining the mechanical properties of the polymer. For example, increasing the crystallinity generally increases Young's modulus and decreases the elongation at break. In other words, increasing the crystallinity of a polymer will make the polymer more brittle. Therefore, there are needs for medical crystalline polymer devices with improved mechanical properties and methods for preparing the same.

SUMMARY OF THE INVENTION

One object of the present invention is to provide a medical polymer device with improved mechanical properties.

Another object of the present invention is to provide a method for preparing said medical polymer device.

Yet another object of the present invention is to provide a method for modifying a medical polymer device comprising a biodegradable polymer.

The objects of the present invention have been achieved by providing the following technical solutions.

In one aspect, the present invention provides a medical polymer device comprising a biodegradable polymer, the biodegradable polymer has a crystallinity of from about 10% to about 80%, and preferably from about 20% to about 60%, wherein the medical polymer device further comprises a small molecule organic compound which diffuses into the biodegradable polymer, the small molecule organic compound has a molecular weight of from about 100 to about 1000 Daltons, preferably from about 150 to about 500 Daltons, and more preferably from about 150 to about 250 Daltons, and the small molecule organic compound is non-evaporating or low-evaporating.

As used herein, the term "non-evaporating or low-evaporating" generally refers to an organic compound having a vapor pressure of no more than 2000 Pa at 25° C.

The inventors have found that the mechanical properties, especially the elongation at break, can be greatly improved by diffusing the small molecule organic compound into the crystalized polymer devices. Accordingly, the brittleness of the polymer devices is therefore significantly reduced.

In the present invention, the small molecule organic compound is preferably a liquid that is capable to dissolve or swell the biodegradable polymer. In some embodiments, the small molecule organic compound is a liquid that is capable to swell the biodegradable polymer. In this case, the small molecule organic compound is also referred to as "a solvent" for the biodegradable polymer.

Without intending to be limited by theory, it is believed that, by carefully choosing the small molecule organic compound, said organic compound molecule will preferably diffuse into the amorphous region of the polymer, leaving the crystalline region intact. In this manner, the crystals (the crystallized region) of the polymer in the polymer matrix can act as physical crosslinking points to maintain the integrity and physical strength of the device. On the other hand, the small molecule present in the amorphous region of the polymer lubricates the polymer chains in the amorphous region of the polymer so that the polymer chains of the polymer with the small molecule move more easily than those of the polymer without the small molecule. In this way, the polymer with the small molecule becomes less brittle.

In some embodiments, the examples of the biodegradable polymers suitable for use in the present invention include, but are not limited to: polylactic acid (PLA), polyglycolic acid (PGA), polycaprolactone (PCL), polyanhydrides, poly(β-hydroxybutyrate), polydioxanone, poly(DTH iminocarbonate), polypropylene fumarate, copolymers thereof and mixtures thereof.

One particularly suitable biodegradable polymer is polylactic acid, which may generally be derived from monomer units of any isomer of lactic acid, such as levorotory-lactic acid ("L-lactic acid"), dextrorotatory-lactic acid ("D-lactic acid"), meso-lactic acid, or mixtures thereof. Monomer units may also be formed from anhydrides of any isomer of lactic acid, including L-lactide, D-lactide, meso-lactide, or mixtures thereof.

In certain embodiments, for example, the biodegradable polymer is poly(L-lactide), polyglycolide, or a copolymer thereof.

Since the small molecule organic compound is designed to essentially stay in the amorphous region, it is required that the small molecule organic compound is of high boiling point or evaporates slowly so that it can stay in the amorphous region for a prolonged period of time to perform its function. As stated above, the small molecule organic compound generally has a vapor pressure of no more than about 2000 Pa at 25° C. In some embodiments, the small molecule organic compound suitable for use in the present invention has a vapor pressure of no more than about 100 Pa at 25° C., and in some embodiments no more than about 7 Pa at 25° C.

In some embodiments, suitable examples of the small molecule organic compound include $C_1$-$C_8$ alkyl salicylate, and in some embodiments, suitable examples of the $C_1$-$C_8$ alkyl can include, but are not limited to: methyl, ethyl, propyl, n-butyl, iso-butyl, pentyl, hexyl and octyl. Similarly, suitable examples of the alkyl salicylate can include, but are not limited to: methyl salicylate, ethyl salicylate, propyl salicylate, n-butyl salicylate, iso-butyl salicylate, pentyl salicylate, hexyl salicylate and octyl salicylate.

In some embodiments, the small molecule organic compound is selected from octyl salicylate, n-butyl salicylate, iso-butyl salicylate, ethyl salicylate, methyl salicylate and a mixture thereof;

and in some embodiments, the small molecule organic compound is a mixture of two or more different small molecule organic compounds selected from octyl salicylate, n-butyl salicylate, iso-butyl salicylate, ethyl salicylate and methyl salicylate.

In some specific embodiments, for examples, the small molecule organic compound is methyl salicylate with a vapor pressure of about 4 Pa at 25° C., and in some specific embodiments, the small molecule organic compound is ethyl salicylate with a vapor pressure of about 6.6 Pa at 25° C.

In some embodiments, the small molecule organic compound is present in an amount of from about 0.1% to about 20% by weight of the biodegradable polymer, preferably from about 0.5% to about 10% by weight of the biodegradable polymer, and more preferably from about 1% to about 5% by weight of the biodegradable polymer.

In some embodiments, the medical polymer device comprises a surgical suture such as a monofilament surgical suture produced by a melt extrusion of a biodegradable polymer, a biodegradable bone screw, a bone plate, a tissue engineering scaffold, a cardiovascular stent used for keeping the blood vessel open for easy blood flow, a bile duct stent, etc.

In some embodiments, the medical polymer device may be configured in any size to accomplish the particular purpose at hand, e.g., in a size suitable for use in bone fixation and repair, cartilage repair, wound closure, cardiovascular devices, endovascular devices, urinary track, esophagus, bile duct, GI track, etc.

In some embodiments, the surface of the device may be further treated by coating means. In this manner, a substance(s) is(are) applied onto the surface that is different from the materials of the device. The substance can be covalently bonded and/or physically absorbed to the surface of the device. Alternatively, the substance can be bonded to the surface of the device through hydrogen bonding, ionic bonding, Van der Waals force or a combination thereof. To increase the stability of the coating (e.g., a biological molecular coating), the coating can be crosslinked using various crosslinking technologies, such as chemical crosslinking, radiation, thermal treatment, or a combination thereof, etc. Further, the crosslinking can take place in a vacuum at an elevated temperature above room temperature. The radiation used for crosslinking can be an e-beam radiation, a gamma radiation, an ultraviolet radiation, or a combination thereof.

In some embodiments, the surface of the device may be coated with a therapeutic agent(s) or a therapeutic composition comprising a therapeutic agent. In a specific embodiment, the therapeutic composition comprises a further polymer and a therapeutic agent(s).

In certain embodiments, for example, polyesters may be employed in the therapeutic composition. A variety of polyesters may generally be employed, such as polycaprolactone, polyesteramides, polylactic acid (PLA) and its copolymers, polyglycolic acid, poly-3-hydroxybutyrate (PHB), poly-3-hydroxyvalerate (PHV), poly-3-hydroxybutyrate-co-4-hydroybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers and so forth. In a specific embodiment, a particularly suitable polymer for use in the therapeutic composition is poly(D-lactide) (PDLA).

In certain embodiments, for instance, the therapeutic agent may be selected from a variety of known classes of compounds. Examples of such therapeutic agent can include, but are not limited to: anti-inflammatory agents, antitumor agents, pain medications (e.g., analgesics), antihistamines, anti-infective agents, wound healing agents (e.g., haemostatics), anti-proliferative agents, peptides, macrolide immunosuppressant (e.g., rapamycin), corticosteroids, elastase inhibitors, antimicrobially active compounds (e.g., antibiotics, antibacterial agents, antifungal agents, etc.), anti-allergic agents, cardiovascular agents, anti-arrhythmic agents, anticoagulants, antihypertensive agents, antineoplastic agents, antioxidants (e.g., Vitamin E), immunosuppressants, antithyroid agents, cardiac inotropic agents, corticosteroids, cough suppressants (expectorants and mucolytics), diuretics, immunological agents, lipid regulating agents, muscle relaxants, oncology therapies, parasympathomimetics, sympathomimetics, thyroid agents, vasodilators, and xanthines.

Particularly suitable therapeutic agents for use in the present invention may include antibiotics, anti-inflammatory agents, antitumor agents, antifungal agents, pain medications, antihistamines, anti-infective agents, wound healing agents, and anti-proliferative agents.

In another aspect, the present invention provides an easy and simple method for preparing the medical polymer device, wherein the method comprises the steps of:

soaking a pre-formed medical polymer device made from a biodegradable polymer having a crystallinity of from about 10% to about 80%, and preferably from about 20% to about 60% in a small molecule organic compound or a solution of a small molecule organic compound and one or more additional substances such that the small molecule organic compound is diffused into the biodegradable polymer; wherein the small molecule organic compound is in a liquid form.

In some embodiments, the pre-formed medical polymer device can be produced by any conventional methods known in the art. Further, the pre-formed medical polymer device can also be commercially available, e.g., from Beijing Advanced Medical Technologies, Co. Ltd of Beijing, China.

In yet another aspect, the present invention provides an easy and simple method for modifying a medical polymer device which is made from a biodegradable polymer having a crystallinity of from about 10% to about 80%, and preferably from about 20% to about 60%, wherein the method comprises the steps of:

soaking the medical polymer device in a small molecule organic compound or a solution of a small molecule organic compound and one or more additional substances such that the small molecule organic compound is diffused into the biodegradable polymer; wherein the small molecule organic compound has a molecular weight of from about 100 to about 1000 Daltons, preferably from about 150 to about 500 Daltons, and more preferably from about 150 to about 250 Daltons, and the small molecule organic compound is in a liquid form and is non-evaporating or low-evaporating.

In the present invention, the small molecule organic compound can be easily and simply diffused into a crystalline polymer device to improve the mechanical properties, and especially, reduce the brittleness of the device through these methods.

In certain embodiments, the medical polymer device is immersed or soaked in an appropriate low evaporation solvent that can preferably diffuse into and stay within the amorphous region of the polymer device comprising struts connected in a pre-designed three-dimensional pattern.

In some embodiments, suitable examples of the additional substances include therapeutic agents, such as antibiotics, anti-inflammatory agents, antitumor agents, antifungal agents, pain medications, antihistamines, anti-infective agents, wound healing agents, or anti-proliferative agents.

In some embodiments, the additional substances constitute about 1 wt % to about 3 wt % of the solution.

In some embodiments, the soaking is carried out at a temperature above the melting point of the small molecule organic compound and below the boiling point temperature of the small molecule organic compound, in some embodiments at a temperature of from about 25° C. to about 80° C., and in some embodiments at a temperature of from about 45° C. to about 70° C.

In some embodiments, the method further comprises the step of removing the external small molecule organic compound from the polymer device after soaking.

BRIEF DESCRIPTION OF THE DRAWINGS

A full and enabling disclosure of the present invention is set forth more particularly in the remainder of the specification, including reference to the accompanying figures, in which.

BEST MODE FOR CARRYING OUT THE INVENTION

Figure 1:
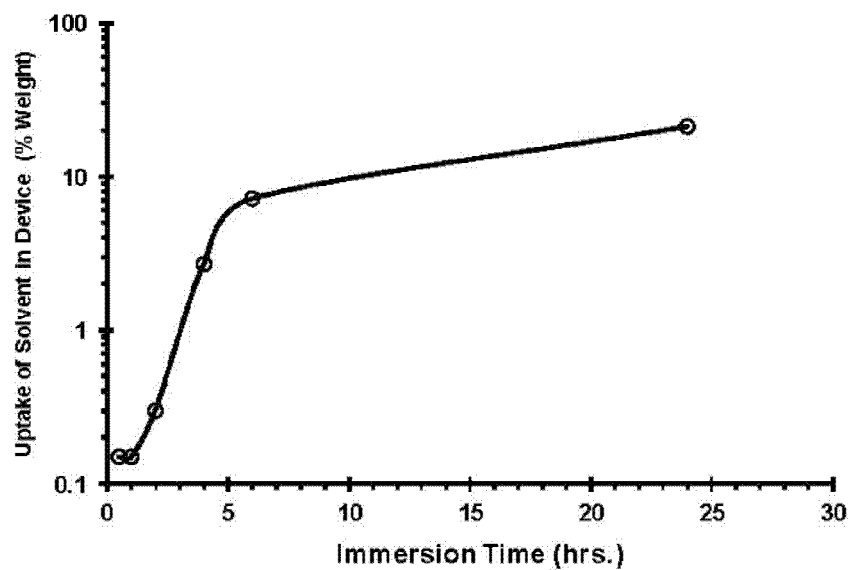
FIG. 1 illustrates the kinetic curve of the controlled infusion of the small molecule organic compound into a polymer device.
Figure 2:
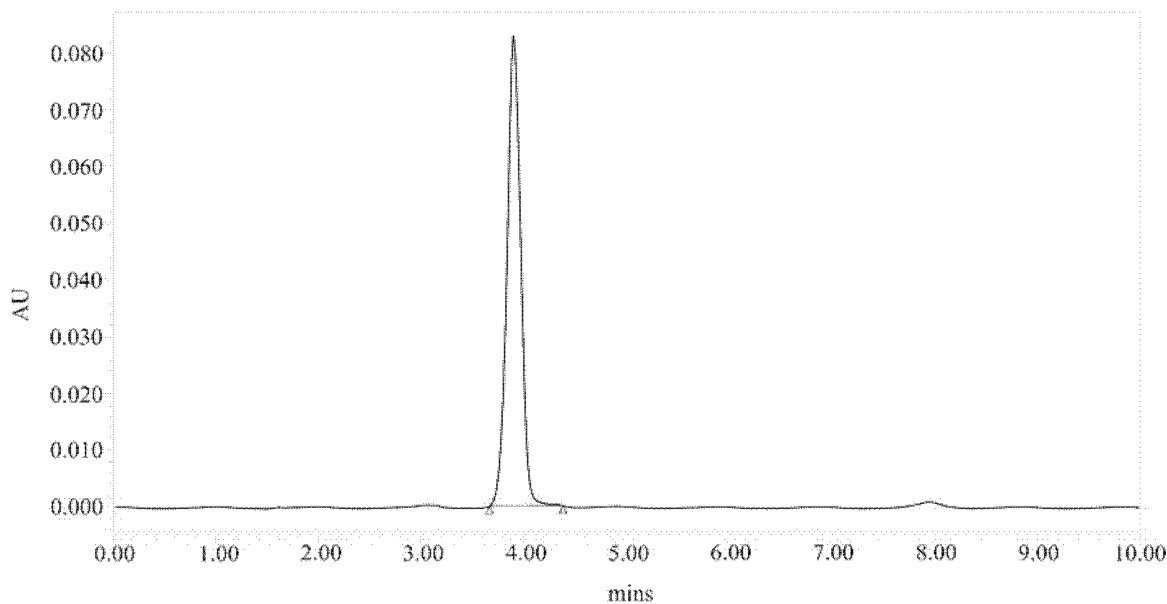
FIG. 2 illustrates an HPLC chromatogram of methanol extract obtained from a methyl salicylate infused stent.
Figure 3:
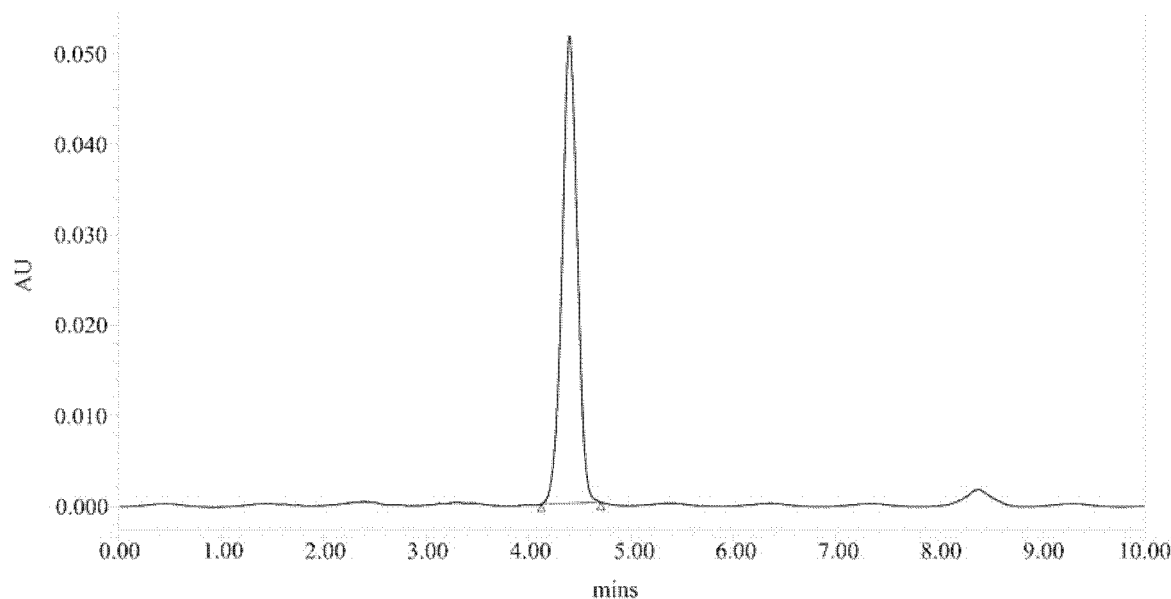
FIG. 3 illustrates an HPLC chromatogram of methanol extract obtained from an ethyl salicylate infused stent.
Figure 4:
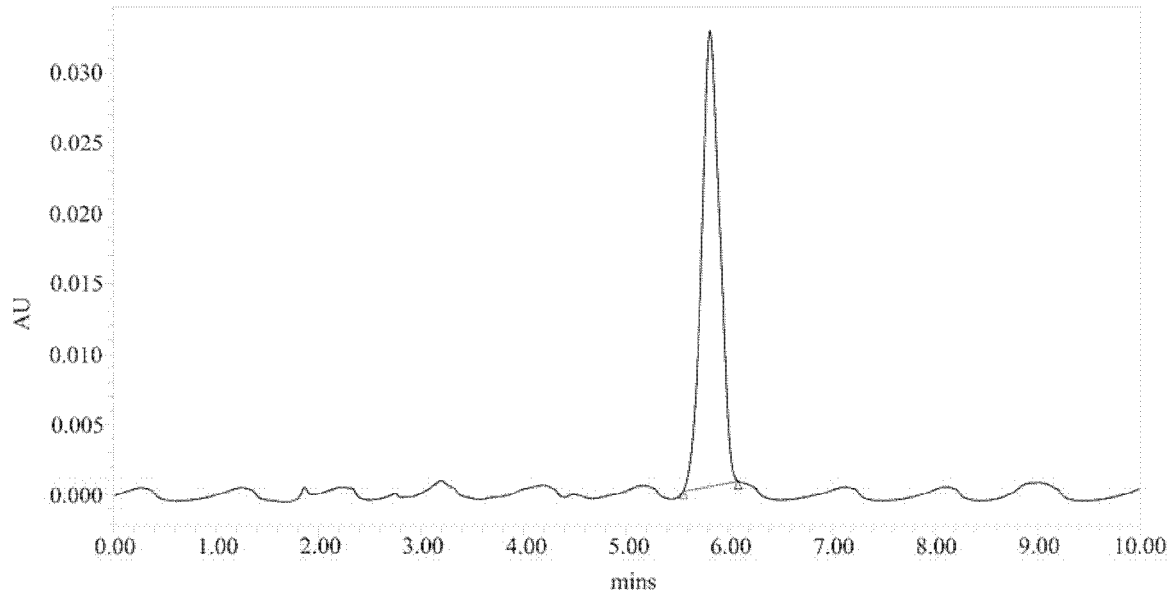
FIG. 4 illustrates an HPLC chromatogram of methanol extract obtained from a n-butyl salicylate infused stent.
Figure 5:
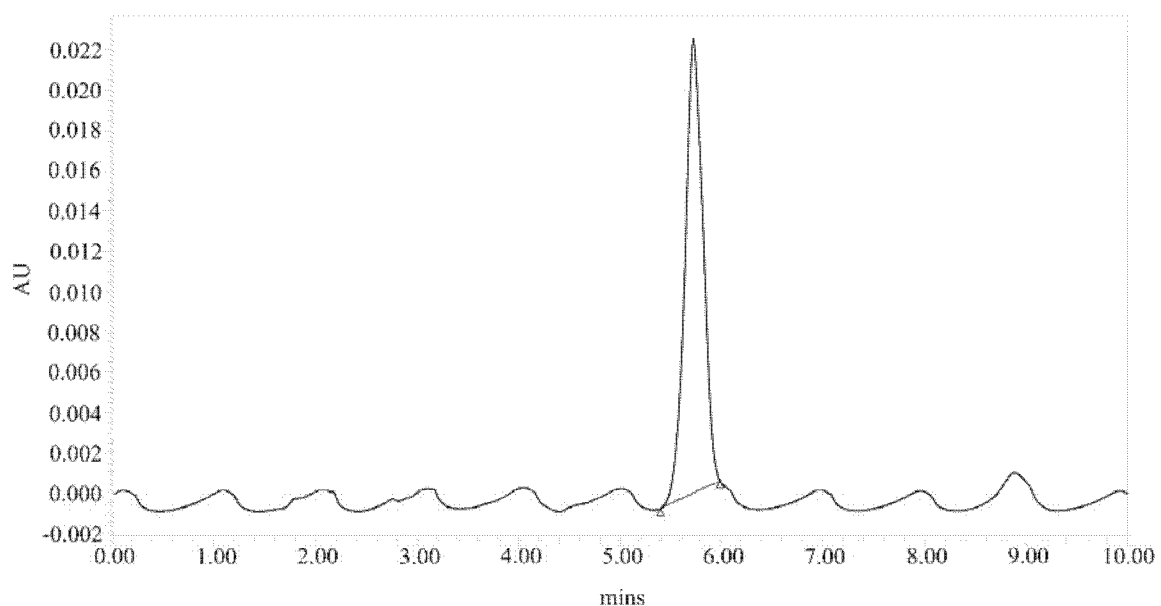
FIG. 5 illustrates an HPLC chromatogram of methanol extract obtained from an iso-butyl salicylate infused stent.

The polymer device used in present invention can be immersed completely in the solvent within a container at a set temperature. A typical weight ratio increase curve is shown in FIG. 1.

The weight increase ratio is calculated as:

$$Q=(W_t-W_o)/W_o\times 100\%$$

Where Q is the weight increase ratio, $W_t$ is the weight of the device at immersion time t, and $W_o$ is the weight of the device before immersion.

By controlling the immersion time, the amount of the solvent diffused into the polymer device can be controlled at a given temperature.

EXAMPLE 1

The diffusion process for the small molecule organic compound infusion into the polymeric device as a function of time.

The kinetics of the small molecule organic compound diffusing into the polymer stent was studied. Intraluminal stents, in the sizes of 6 mm in diameter and 36 mm in length, were made by braiding a single PLLA fiber with a crystallinity of 30% on a mandrel. Three stents were studied. Each stent was immersed in 10 ml liquid of ethyl salicylate for 24 hours at 55 C. At different time intervals the stents were taken out, rinsed briefly with ethanol and padded dry with drying cloth. The weight of stents was then measured by a high accuracy stent balance (METTLER XP-6). FIG. 1 shows the kinetic curve of ethyl salicylate uptake in the stent as a function of time.

EXAMPLE 2

Treatment of a surgical poly(L-lactide)(PLLA) monofilament suture.

A PLLA mono filament suture with a diameter of 150 micrometer was produced using a polymer extruder equipped with a 200 micrometer diameter nozzle. The PLLA suture has a crystallinity about 20%. The PLLA suture was completely immersed in n-butyl salicylate at 70° C. for 5 hours. The weight increase ratio of the device is 3%. A tensile test using sample length of 76 mm and pulling speed of 127 mm/min was performed on the fibers with and without the n-butyl salicylate infusion treatment. The results showed that the small molecule infusion treatment had a significant effect on the break elongation of the PLLA suture which increased from 10% to 105% due to the treatment as shown in Table 1.

TABLE 1

Effect of Small Molecule Infusion on the Mechanical Property of PLLA Fibers

| Tensile Parameter | Fibers Without Treatment | Fibers With Treatment |
| --- | --- | --- |
| Young's Modulus (GPa) | 10.6 | 5.5 |
| Yield Strength (MPa) | 250 | 193 |
| Break Strength (MPa) | 263 | 247 |
| Break Elongation (%) | 10.2 | 104.5 |

EXAMPLE 3

The presence of the small molecule organic compound infused into a PLLA-made device after immersion in the solvent was identified and quantified by high performance liquid chromatography (HPLC) using the method described as follows.

Intraluminal stents, in the sizes of 3 mm in diameter and 13-18 mm in length, were made by braiding a single PLLA fiber on a mandrel. The stents were immersed respectively in 5 ml liquids of methyl salicylate, ethyl salicylate, n-butyl salicylate and iso-butyl salicylate for 2 hours at 50° C. The stents were removed off the excessive liquids by drying cloth and further dried in vacuum at 45° C. for several hours till the weight gains became constant. The treated and dried stents were then extracted in 10 ml methanol. The aliquots of extracts were analyzed by HPLC using a solvent mixture of acetonitrile and water running at 0.8:0.2 ml/s ratio at 40° C. The HPLC chromatograms that identify the elution peaks for methyl salicylate (3.9 min), ethyl salicylate (4.4 min), n-butyl salicylate (5.8 min) and iso-butyl salicylate (5.7 min) in the extracts are shown in FIGS. 2-5.

TABLE 2

Small Molecule Organic Compound Infusion into Stent Measured by HPLC

| Infusion Molecules | The weight of the stent (μg) | Amount of Solvent Infused into Stent Measured by HPLC (μg) | The weight increment percent (%) |
|---|---|---|---|
| Methyl Salicylate | 2400 | 480 | 20.0% |
| Ethyl Salicylate | 2400 | 312 | 13.0% |
| n-Butyl Salicylate | 2400 | 346 | 14.4% |
| iso-Butyl Salicylate | 2400 | 230 | 9.6% |

EXAMPLE 4

The presence of the small molecule organic compound infused into a polyglycolide-made device after immersion in the solvent was identified and quantified by high performance liquid chromatography (HPLC) using the method described as follows.

Intraluminal stents, in the sizes of 3 mm in diameter and 13-18 mm in length, were made by braiding a single polyglycolide fiber on a mandrel. The weight of stents before immersion was then measured by a high accuracy stent balance (METTLER XP-6). The stents were immersed respectively in 5 ml liquids of methyl salicylate, ethyl salicylate, n-butyl salicylate and iso-butyl salicylate for 2 hours at 50° C. The stents were removed off the excessive liquids by drying cloth and further dried in vacuum at 45° C. for several hours till the weight gains became constant. The weight of stents was then measured by a high accuracy stent balance (METTLER XP-6).

TABLE 3

Small Molecule Infusion into Stent Measured by a high accuracy stent balance

| Infusion Molecules | Weight Gain of Stent After Immersion Treatment (μg) | The weight increment percent (%) |
|---|---|---|
| Methyl Salicylate | 468 | 18.7% |
| Ethyl Salicylate | 337 | 13.5% |
| n-Butyl Salicylate | 275 | 11.0% |
| iso-Butyl Salicylate | 237 | 9.5% |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

The invention claimed is:

1. A medical polymer device comprising:
 a biodegradable polymer having a crystallinity of 10% to 80%; and
 a small molecule organic compound diffused into the biodegradable polymer, the small molecule organic compound having a molecular weight of 100 to 1000 Daltons;
 wherein
  amorphous regions of the biodegradable polymer have a higher concentration of the small molecule organic compound than crystalline regions of the biodegradable polymer,
  the small molecule organic compound is non-evaporating or low-evaporating,
  the small molecule organic compound is a $C_1$-$C_8$ alkyl salicylate,
  the small molecule organic compound is present in an amount of 0.1% to 20% by weight of the biodegradable polymer.

2. The medical polymer device of claim 1, wherein the biodegradable polymer has a crystallinity of 20% to 60%.

3. The medical polymer device of claim 1, wherein the small molecule organic compound has a molecular weight of 150 to 250 Daltons.

4. The medical polymer device of claim 1, wherein the biodegradable polymer is selected from the group consisting of polylactic acid, polyglycolic acid, polycaprolactone, polyanhydrides, poly(β-hydroxybutyrate), polydioxanone, poly(DTH iminocarbonate), polypropylene fumarate, copolymers thereof, and mixtures thereof.

5. The medical polymer device of claim 1, wherein the biodegradable polymer is poly (L-lactide), polyglycolide, or a copolymer thereof.

6. The medical polymer device of claim 1, wherein the small molecule organic compound has a vapor pressure of no more than 2000 Pa at 25° C.

7. The medical polymer device of claim 1, wherein the small molecule organic compound is one or a mixture of two or more small molecule organic compounds selected from the group consisting of octyl salicylate, n-butyl salicylate, iso-butyl salicylate, ethyl salicylate, and methyl salicylate.

8. The medical polymer device of claim 1, wherein the small molecule organic compound is present in an amount of 0.5% to 10% by weight of the biodegradable polymer.

9. The medical polymer device of claim 1, wherein the surface of the device is coated with a therapeutic agent or a therapeutic composition comprising the therapeutic agent.

10. The medical polymer device of claim 9, wherein the therapeutic agent is selected from the group consisting of antibiotics, anti-inflammatory agents, antitumor agents, antifungal agents, pain medications, antihistamines, anti-infective agents, wound healing agents, anti-proliferative agents, and mixtures thereof.

11. The medical polymer device of claim 1, wherein the composition comprises a further polymer, wherein the further polymer is selected from the group consisting of polycaprolactone, polyesteramides, polylactic acid and its copolymers, polyglycolic acid, poly-3-hydroxybutyrate, poly-3-hydroxyvalerate, poly-3-hydroxybutyrate-co-4-hydroybutyrate, poly-3-hydroxybutyrate-co-3-hydroxyvalerate copolymers, poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, succinate-based aliphatic polymers, and mixtures thereof.

12. The medical polymer device of claim 1, wherein the medical polymer device is a surgical suture, a biodegradable bone screw, a bone plate, a tissue engineering scaffold, or a cardiovascular stent.

13. A method for preparing the medical polymer device of claim 1, wherein the method comprises:
soaking a pre-formed medical polymer device made from a biodegradable polymer having a crystallinity of 10% to 80% in a small molecule organic compound or a solution of a small molecule organic compound and one or more optional additional substances such that the small molecule organic compound is diffused into the biodegradable polymer, wherein the small molecule organic compound is in a liquid form, to form the medical polymer device comprising
the biodegradable polymer having a crystallinity of 10% to 80%, and
the small molecule organic compound diffused into the biodegradable polymer, the small molecule organic compound having a molecular weight of 100 to 1000 Daltons, wherein the small molecule organic compound is non-evaporating or low-evaporating, the small molecule organic compound is a $C_1$-$C_8$ alkyl salicylate, and the small molecule organic compound is present in an amount of 0.1% to 20% by weight of the biodegradable polymer.

14. The method of claim 13, wherein the soaking is carried out at a temperature above the melting point of the small molecule organic compound and below the boiling point temperature of the small molecule organic compound.

15. The method of claim 13, wherein the method further comprises removing the external small molecule organic compound from the polymer device after soaking.

\* \* \* \* \*